US00PP32237P2

(12) United States Plant Patent
Valin

(10) Patent No.: US PP32,237 P2
(45) Date of Patent: Sep. 29, 2020

(54) ***WEIGELA* PLANT NAMED 'TMWG16-02'**

(50) Latin Name: *Weigela florida*
Varietal Denomination: TMWG16-02

(71) Applicant: Branded Garden Products Ltd., Ipswich (GB)

(72) Inventor: Charles Valin, Ipswich (GB)

(73) Assignee: Branded Garden Products Ltd., Ipswich (GB)

( * ) Notice: Subject to any disclaimer, the term of this patent is extended or adjusted under 35 U.S.C. 154(b) by 43 days.

(21) Appl. No.: 16/501,908

(22) Filed: Jul. 2, 2019

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — Barbara Campbell; Cochran Freund & Young LLC

(57) ABSTRACT

A new variety of *Weigela florida* plant named 'TMWG16-02' that is characterized by upright narrow vase-shaped plant habit, pale pink and mid-pink colored flowers which are borne profusely and continuously in early and mid-spring and then sporadically during summer, in clusters along the entire length of the stem, is disclosed.

2 Drawing Sheets

Genus and species: *Weigela florida.*
Variety denomination: 'TMWG16-02'.

BACKGROUND OF THE NEW PLANT

The present invention relates to a new and distinct cultivar of *Weigela*, grown as an ornamental plant for use in the garden and landscape. The new variety is known botanically as *Weigela florida* and will be referred to hereinafter by the cultivar name 'TMWG16-02'.

Whereas cultivars of *Weigela florida* in commerce have typically been bred for low compact plant habit, 'TMWG16-02' was developed and selected by the inventor for its unique combination of upright plant habit and profuse flowering along the entire stem.

'TMWG16-02' arose from an open-pollination in Summer 2014 of the inventor's proprietary seedling *Weigela florida* 'WG13001' (female parent, unreleased and unpatented) in Ipswich, Suffolk, United Kingdom. The identity of the *Weigela florida* male parent is unknown. 'TMWG16-02' was selected in 2016 in Ipswich, Suffolk, United Kingdom. 'TMWG16-02' was grown at a greenhouse and field nursery in Ipswich, Suffolk, United Kingdom.

'TMWG16-02' was first asexually reproduced in Ipswich, Suffolk, United Kingdom in 2016 by softwood cuttings. Since that time, the unique characteristics of the new *Weigela* plant have been uniform, stable and reproduced true to type in successive generations of asexual reproduction via softwood cuttings.

SUMMARY

The following traits have been repeatedly observed and represent the characteristics of the new *Weigela* variety 'TMWG16-02'. 'TMWG16-02' has not been tested under all possible conditions and phenotypic differences may be observed with variations in environmental, climatic and cultural conditions, however, without any variance in genotype.

1. 'TMWG16-02' exhibits an upright narrow vase-shaped plant habit.
2. After two years of growth in a 3-gallon container, plants of 'TMWG16-02' achieve a height of 90 cm to 120 cm and a width (at full height) of 45 cm to 60 cm.
3. A mature plant of 'TMWG16-02' which is growing in-ground achieves a height of 180 cm to 200 cm and a width at full height of 90 cm to 120 cm.
4. The flower buds of 'TMWG16-02' are pink in color.
5. The flowers of 'TMWG16-02' are mid-pink in color when freshly opened.
6. The flowers of 'TMWG16-02' become paler pink with age, eventually very pale lilac-pink.
7. The flowers of 'TMWG16-02' are borne in clusters along the entire length of the stem.
8. 'TMWG16-02' flowers profusely and continuously in early and mid-spring and then sporadically during summer.
9. The foliage of 'TMWG16-02' is mid green in color.
10. 'TMWG16-02' grows well in moist well-drained soils in full sun to partial shade.
11. 'TMWG16-02' is hardy at least to USDA Zone 6.

BRIEF DESCRIPTION OF THE PHOTOGRAPHS

The accompanying color photographs illustrate the overall appearance of the new *Weigela* variety 'TMWG16-02' showing colors as true as it is reasonably possible to obtain in colored reproductions of this type. Colors in the photographs may differ from the color values cited in the detailed botanical description, which accurately describe the actual colors of the new variety 'TMWG16-02'.

Figure 1:
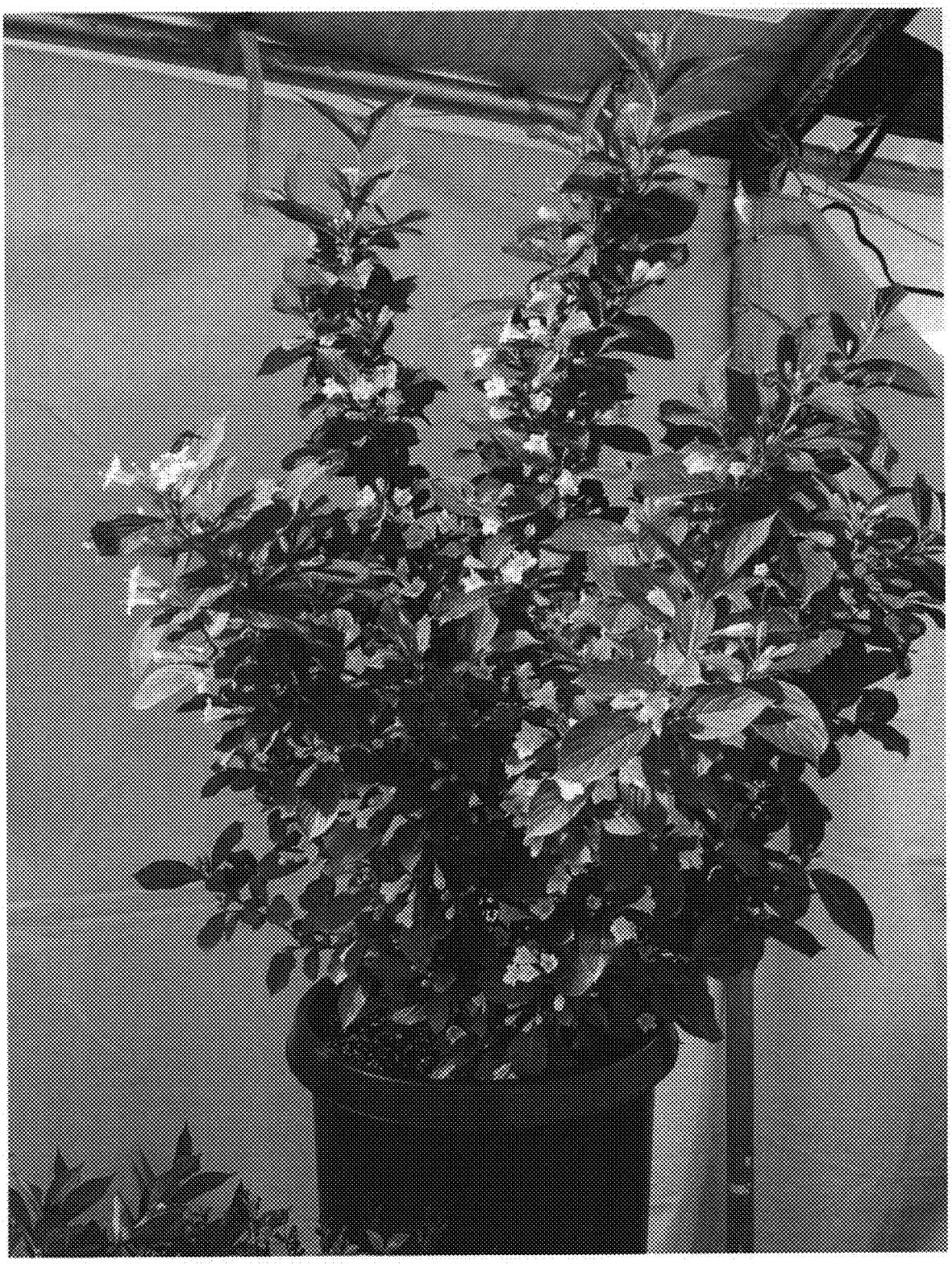
FIG. 1 depicts a whole plant of 'TMWG16-02' in bud and flower.
Figure 2:
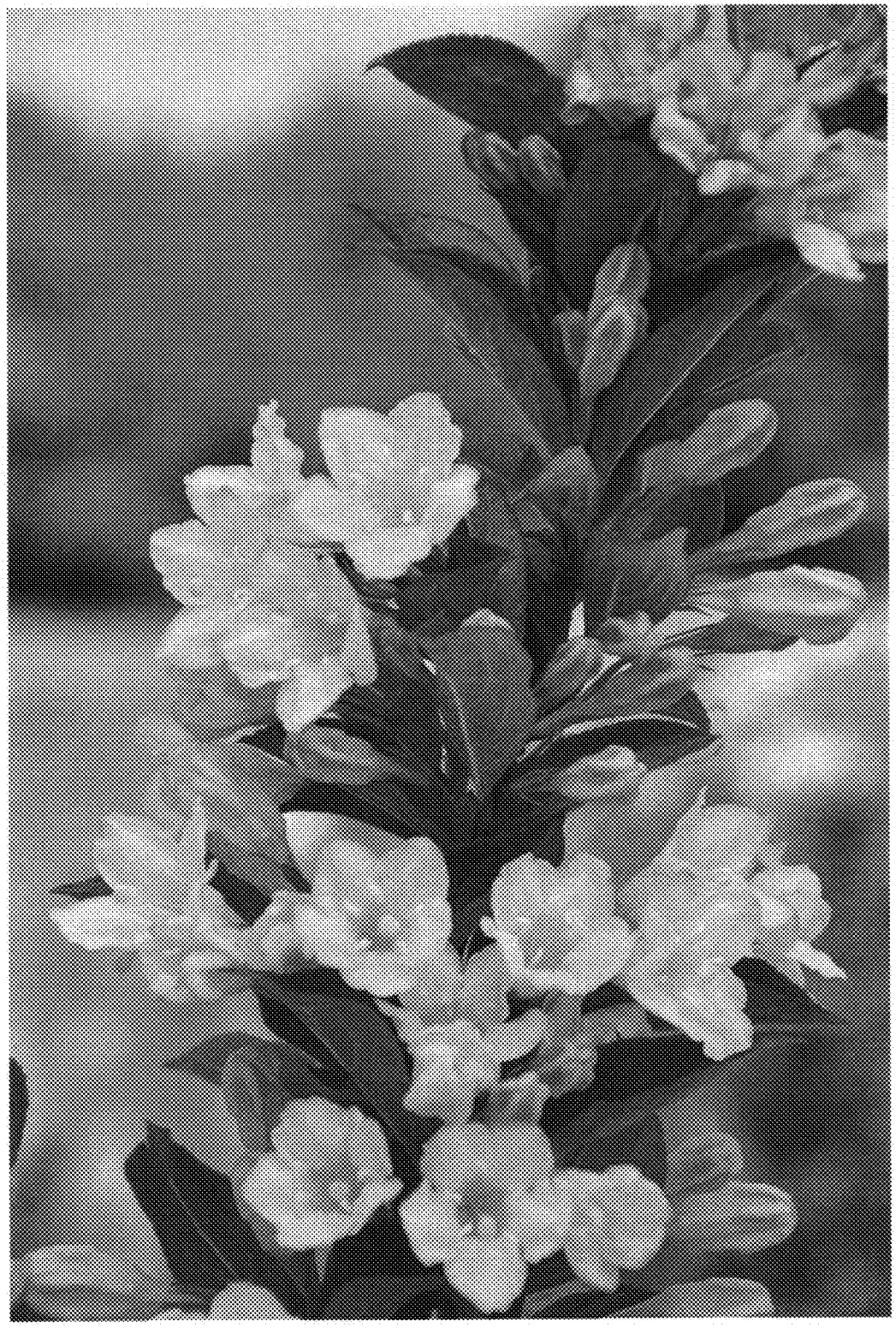
FIG. 2 depicts a close-up view of the buds and flowers of 'TMWG16-02' at peak flowering.

Photographs were taken in Oxnard, Calif. from a two-year-old plant which was grown outdoors in a 3-gallon container. No chemicals were used to treat the plant. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'TMWG16-02'. Data was collected from two-year old plants grown in 3-gallon containers in Oxnard, Calif. The color determinations are in accordance with the 2007 edition of The Colour Chart of The Royal Horticultural Society, London, England, except where general color terms of ordinary dictionary significance are used. No chemicals were used to treat the plants. Growing conditions are typical of other *Weigela*.

Botanical classification: *Weigela*.

*Variety*.—'TMWG16-02'.

*Species*.—*Florida*.

Parentage: 'TMWG16-02' was raised from seed collected from *Weigela florida* 'WG13001' as open-pollinated female parent. The identity of the *Weigela florida* male parent is unknown.

Plant description:

*Growth habit*.—Upright, narrow vase shaped.

*Use*.—In containers and in the landscape; may be grown on canes or on a trellis to produce a more markedly columnar plant habit.

*Suitable container sizes*.—1 to 3-gallon containers.

*Dimensions in second year (the observed plants) in a 3-gallon container*.—90 cm to 120 cm in height, and 45 cm to 60 cm in width measured at full plant height.

*Dimensions when mature in open ground*.—180 cm to 200 cm in height, 90 cm to 120 cm in width measured at full plant height.

*Hardiness*.—At least hardy to USDA Zone 6.

*Propagation*.—Stem cuttings.

*Time to initiate roots*.—5 to 6 weeks are required to produce roots on an initial cutting.

*Crop time*.—One year to 18 months are required to produce a finished one-gallon container from a rooted cutting.

*Root system*.—Fibrous.

*Light*.—Plant in full sun or partial shade.

*Soil*.—Plant in moist but well-drained soil.

*Type*.—Deciduous shrub.

*Seasonal interest*.—A combination of pale pink and mid-pink flowers in early and mid-spring and periodically through summer.

Stem:

*Shape*.—Terete.

*Dimensions*.—15 cm to 20 cm in length, 1 cm diameter at soil level.

*Color*.—198A.

*Surface*.—Lignified in second year, rough, glabrous, lenticels present.

*Lenticels*.—Spaced approximately 5 mm apart, roughly circular, diameter is 2 mm, raised 1 mm, color is 196C.

Branches:

*Branch stem dimensions*.—60 cm to 90 cm in length, 5 mm to 8 mm in diameter.

*Shape*.—Square with rounded edges.

*Internode length*.—5 cm to 8 cm.

*Color*.—146C with longitudinal streaks 178B.

*Surface*.—Smooth, puberulent, hairs fine, white.

Foliage:

*Leaf arrangement*.—Opposite.

*Leaf division*.—Simple.

*Leaf shape*.—Ovate, slightly recurved.

*Leaf attachment*.—Sessile or very short petiolate.

*Petiole dimensions (where present)*.—2 mm in length and 2 mm in width.

*Petiole color*.—Ranges between 137B and 138B.

*Leaf dimensions*.—85 mm in length, 35 mm in width.

*Leaf surface (adaxial)*.—Glabrous.

*Leaf surface (abaxial)*.—Glabrous, pubescent, hairs fine, 1 mm to 2 mm in length, color is white.

*Leaf color, spring and summer (adaxial surface)*.—137B.

*Leaf color, spring and summer (abaxial surface)*.—138B.

*Leaf color, fall (both surfaces)*.—Initially 139C then ranging though N144B, 151A to 163B.

*Leaf apex*.—Acute, occasionally acuminate.

*Leaf base*.—Rounded.

*Leaf margin*.—Finely serrate, glabrous except leaf margin pubescent towards base, hair color white, hair length 1 mm to 2 mm.

*Leaf venation pattern*.—Pinnate.

*Veins (adaxial surface)*.—Prominent midrib, slightly depressed, color is 155A.

*Veins (abaxial surface)*.—Prominent midrib and lateral veins, raised approximately 1 mm, color ranges between 155A and 160C.

Inflorescence:

*Inflorescence form*.—Cymose. Present at each leaf axil.

*Quantity of flowers per inflorescence*.—2 to 5.

*Time and duration of flowering*.—Beginning in late April or early May according to climate and season, lasting until July.

Flowers:

*Flower aspect*.—Outward and upward facing.

*Diameter of fully developed flower (at flower tube apex)*.—25 mm to 28 mm.

*Length of flower*.—35 mm.

*Bud*.—Shape: Cylindrical, apex capitate. Color (first emergence): 49A. Color (immediately prior to opening): 49C. Dimensions: 30 mm in length, 10 mm immediately prior to opening. Surface: Tomentose.

*Bracteoles*.—Arrangement: Uneven pair located at the base of peduncle. Shape: Narrowly lanceolate. Dimensions: Longer bracteole 12 mm to 15 mm in length, 2 mm to 3 mm in width; shorter bracteole 5 mm to 8 mm in length, 2 mm in width. Color: N144C. Surface: Glabrous.

*Peduncle*.—Dimensions: 15 mm to 18 mm in length and 2 mm to 3 mm in diameter. Shape: Terete. Color: 144C. Surface: Puberulent, hairs fine, white.

*Calyx, sepals*.—Shape: Funnel-shaped. Calyx diameter: 4 mm. Sepals: 5 in number, occasionally in semi-fused pairs. Sepal dimensions: 8 mm to 10 mm in length, 2 mm in width. Sepal color (both surfaces): 163B. Sepal surface (both surfaces): Lightly pubescent.

*Corolla*.—Shape: Salverform. Dimensions: 30 mm in length, 2 mm in diameter at base, 12 mm in diameter at base of petal lobes. Surface: Glabrous. Tube color (flower freshly opened): Adaxial surface: 49. Abaxial surface: NN155D. Tube color (flower fully developed, 3 to 5 days after first opening): Both surfaces: 55A.

*Petals*.—Number: 5, fused. Shape: Equal, orbicular. Color: (flower freshly opened): Both surfaces: 55A. Color (flower fully developed, and aging): Adaxial surface: 49B, aging to very pale pink-lilac, between (but paler than) 75D and 76D. Abaxial surface (all ages): 75D and 76D, but paler. Petal margins 49B towards apex. Surface texture: Glabrous.

Reproductive organs:

*Number of stamens*.—5, fused at base.

*Dimensions*.—15 mm in length and less than 1 mm in diameter.

*Filament color*.—54A.

*Anther shape*.—Bifid, narrow elliptical.

*Anther dimensions*.—4 mm in length and 1 mm in width.

*Anther color*.—159C.

*Pollen color*.—NN155C.

*Pollen amount*.—Minimal.

*Number of pistils*.—1.

*Style*.—Terete, 28 mm in length and 1 mm in width.

*Style color*.—62B.

*Style surface*.—Glabrous.

*Stigma shape*.—Capitate, three-lobed.

*Stigma dimensions*.—4 mm in width and 2 mm in depth.

*Stigma color*.—NN155B.

*Ovary*.—Superior, ovoid, 5 mm in length and 2.5 mm in diameter, color is 145C, smooth.

Fruit: Cylindrical, 12 mm to 15 mm in length, 5 mm in diameter. Surface, glaucous with tiny protrusions. Color initially 137A becoming 185A when dry and ripe. Capsules, 2, longitudinal.

Seed: Shape, ovoid, length 1.5 mm, diameter 1 mm, color 163B to 163C, surface, rough.

Susceptibility or resistance to pests and diseases: None observed.

COMPARISON WITH PARENTAL LINE

In comparison with the female parent, the proprietary seedling *Weigela florida* 'WG13001', 'TMWG16-02' exhibits a very upright growth and heavy flowering all along its stems. The identity and characteristics of the male parent are unknown.

COMPARISON WITH CLOSEST KNOWN VARIETY

The closest comparison variety known to the inventor is 'TMWG16-04' (U.S. application Ser. No. 16/501,910). Whereas both 'TMWG16-02' and 'TMWG16-04' exhibit markedly upright plant habits with flowers borne along their entire length of their stems, the flowers of 'TMWG16-02' are pink in color, and the flowers of 'TMWG16-04' are scarlet in color. In addition, 'TMWG16-02' is much earlier to come into flower, typically 4 weeks before the first flowering of 'TMWG16-04'

I claim:

1. A new and distinct cultivar of *Weigela* plant named 'TMWG16-02' as described and illustrated herein.

* * * * *